United States Patent [19]

Stansbury

[11] Patent Number: 5,463,008
[45] Date of Patent: Oct. 31, 1995

[54] MONOMERS FOR DOUBLE RING-OPENING POLYMERIZATION WITH EXPANSION

[75] Inventor: Jeffrey W. Stansbury, Gaithersburg, Md.

[73] Assignee: The United States of America as represented by the Secretary of Commerce, Washington, D.C.

[21] Appl. No.: 273,753

[22] Filed: Jul. 12, 1994

Related U.S. Application Data

[62] Division of Ser. No. 846,480, Mar. 6, 1992, Pat. No. 5,362,889.

[51] Int. Cl.$^6$ .............................. C08F 24/00; C08F 20/30
[52] U.S. Cl. .......................................... 526/268; 526/328.5
[58] Field of Search .................................. 526/268, 328.5

[56] References Cited

U.S. PATENT DOCUMENTS 4,387,215  6/1983  Bailey .
4,980,109  12/1990  Yamamoto et al. .

FOREIGN PATENT DOCUMENTS 59-155384  9/1984  Japan .

OTHER PUBLICATIONS

H. Tagoshi, T. Endo, Journal of Polymer Science: Part A: Polymer Chemistry 27, 1415–1418, 1989.
Jeffrey Wilson Stansbury, Dissertation for Ph.D. 1988, University of Maryland.
J. W. Stansbury, J. Dent. Res. 71 (7): 1408–1412, Jul. 1992.
*Journal of Polymer Science: Part A: Polymer Chemistry*, vol. 28, 3529–3532 (1990), John Wiley & Sons, Inc., "Preparation and Radical Polymerization of Spiroorthocarbonate Having 1,3-Dioxolane Skeleton".
*Journal of Polymer Science: Part A: Polymer Chemistry*, vol. 27, 1415–1418 (1989), John Wiley & Sons, Inc., "Radical Polymerization of Unsaturated Spiroorthocarbonate".
Journal of Polymer Science, Polymer Chemistry Ed. 20:1401–1409 (1982), Fukada et al., "Spontaneous Copolymerization of 4-Methylene-1,3-Dioxolanes with Maleic Anhydride".
Journal of Polymer Science, Polymer Chemistry Ed. 13:2525–2530 (1975), Endo et al., "Synthesis and Radical Ring-Opening Polymerization of Spiro-o-Carbonates".
Journal of Polymer Science, Part A, Polymer Chemistry, 27:1415–1418 (1989), Tagoshi et al., "Radical Polymerization of Unsaturated Spiroorthocarbonate".
J Dent Res 58(5):1522–1532, May 1979, Thompson et al., "Dental Resins with Reduced Shrinkage During Hardening".
ACS Polym. Prepr., vol. 31, No. 2, Aug. 1990, Washington, D.C., Wang et al., "Synthesis and Free Radical Ring-Opening Polymerization of 2-Alkyl-7-Methylene-1, 4,6-Trioxapiro[4,4]Nonane".
J Dent Res 66(11):1636–1639, Nov. 1987, Feilzer et al., "Setting Stress in Composite Resin in Relation to Configuration of the Restoration".
Dent Mater 6:167–171, Jul. 1990, Feilzer et al., "Quantitative determination of stress reduction by flow in composite restorations".
Progress in Biomedical Polymers, Plenum Press, New York, 1990, Stansbury et al., "Evaluation of Spiro Orthocarbonate Monomers Capable of Polymerization with Expansion as Ingredients in Dental Composite Materials" pp. 133–139.
J Dent Res 66(3):716–721, Mar. 1987, Zidan et al., "A Comparative Study of the Effects of Dentinal Bonding Agents and Application Techniques on Marginal Caps in Class V Cavities".
J Dent Res 65:219 Abst. #452 (1986), Stansbury et al., "Synthesis of Monomers that Polymerize with Expansion in Volume".
Dissertation of Jeffrey Wilson Stansbury, Ph.D., 1988, "Free Radical Ring-Opening Polymerization of Unsaturated, Asymmetric Spiro Orthocarbonates".

*Primary Examiner*—Joseph L. Schofer
*Assistant Examiner*—Wu C. Cheng
*Attorney, Agent, or Firm*—Stevens, Davis, Miller & Mosher

[57] ABSTRACT

A method of preparing a polymerizate from a reactant monomer of prepolymer which undergoes shrinkage during the formation of said polymerizate which comprises reacting said reactant monomer or prepolymer in the presence of a monomer selected from the group consisting of:

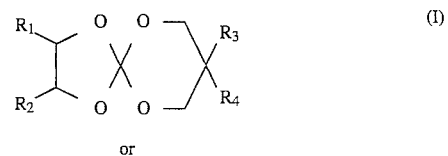

(I)

or

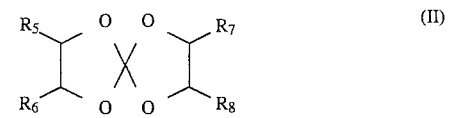

(II)

wherein $R_1$-$R_8$ are as defined herein to form a polymerizate containgin said reactant monomer or prepolymer as chemically contained constituents thereof, and resinous compositions and composites as well as polymers polymerized from such monomers or prepolymers.

13 Claims, 1 Drawing Sheet

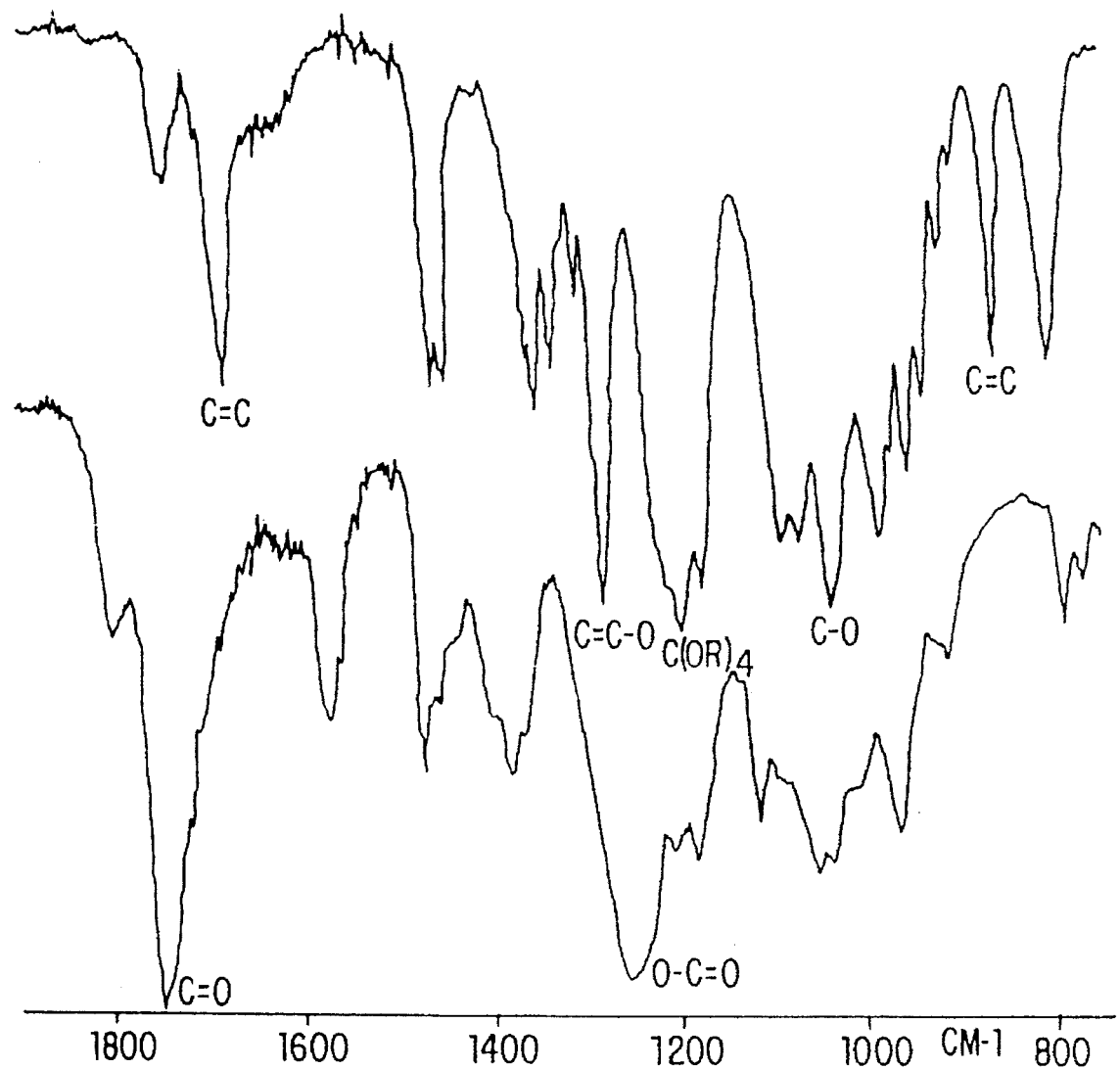

6,463,008

MONOMERS FOR DOUBLE RING-OPENING POLYMERIZATION WITH EXPANSION

This is a division of application Ser. No. 07/846,480, filed Mar. 6, 1992, now U.S. Pat. No. 5,362,889.

BACKGROUND OF THE INVENTION

1. Field of the Invention

The invention relates to a newly developed class of spiro orthocarbonate (SOC) monomers which can undergo double ring-opening polymerization with an expansion in volume. These new monomers offer significant improvements over previously known SOC monomers and have particular utility in compositions including conventional dimethacrylate dental monomers. The SOC monomers of the invention undergo double ring-opening polymerization where two bonds are broken for each new bond formed with a resulting expansion in volume that counters the volume contractions associated with shrinkage of the resinous component(s) of the composition. The resulting polymerized resins exhibit higher adhesive strength to the substrates to which they are bonded.

2. Description of the Prior Art

A wide variety of material deficiencies have been attributed to the volume contraction associated with the polymerization of resins in composite and adhesive applications, especially in the field of dental resins. These problems arose from the generation of stresses which are of sufficient magnitude to cause defects within the resin matrix and debonding at the interfaces. See Feilzer et al., "Setting Stress in Composite Resin in Relation to Configuration of the Restoration", *J. Dent Res*, 66:1636–1639 (1987); Feilzer et al., "Quantitative Determination of Stress Reduction by Flow in Composite Restorations", *Dent Mater*, 6:167–175 (1990); and Zindan et al., "A Comparative Study of the Effects of Dentinal Bonding Agents and Application Techniques on Marginal Gaps in Class V Cavities", *J. Dent Res*, 66:716–721 (1987). These complications undermine performance and often restrict those situations for which compositions and other related dental resin materials can be considered. One approach toward minimizing the extent of polymerization shrinkage in resins is to incorporate free-radically polymerizable spiro orthocarbonate monomers into formulations with conventional dimethacrylate dental monomers. The spirocyclic monomers can undergo double ring-opening polymerization wherein two bonds are broken for each new bond formed. The result is an expansion in volume that can be applied to counter the volume contraction.

While double ring-opening polymerization of SOC monomers has previously been disclosed in U.S. Pat. No. 4,387,215 to Bailey, the utility of those types of monomers in free radical polymerization has been severely limited by their relative lack of reactivity with conventional comonomers and their reluctance to undergo the desired ring-opening process when they do react. Other experience with spiro orthocarbonate monomers formulated into dental resins has demonstrated some distinct advantages. Thompson et al., "Dental Resins with Reduced Shrinkage During Hardening", *J. Dent Res*, 58:1522–1532 (1979) evaluated a relatively high melting, symmetrical spirocyclic monomer included as a slurry in resin compositions. The melting and subsequent ring-opening of the spiro monomer during the polymerization yielded a nearly volume-neutral curing process overall and resulted in a doubling of the adhesive strength of the resin to etched enamel as compared with a control. However, a large proportion of the crystalline spiro component was left undissolved and unreacted in the resin cured at ambient temperature.

These early results led to the development of free-radically polymerizable, asymmetric spiro orthocarbonate monomers, See Endo et al., "Synthesis and Radical Ring-Opening Polymerization of Spiro o-Carbonates", *J. Polym. Sci, Polym Chem Ed*, 13:2525–2530 (1975) and Stansbury et al., "Synthesis of Monomers that Polymerize with Expansion in Volume", *J. Dent Res*, 65:219, Abst. No. 452 (1986), which can have melting points below room temperature depending on substituent and ring size considerations. Liquid spirocyclic monomers were substituted in place of the dimethacrylate diluent monomer in dental composite formulations, See Stansbury et al., "Evaluation of Spiro Orthocarbonate Monomers Capable of Polymerization with Expansion as Ingredients in Dental Composite Materials", *Progress in Biomedical Polymers*, C. G. Cabelein and R. L. Dunn, Eds., New York: Plenum Press, pp. 133–139 (1990). These experimental materials provided polymerization shrinkage values as much as 40% less than that of the control along with a corresponding three-fold increase in the adhesive strength measured between the composite and stainless steel. The disclosures of each of the foregoing publications are herein incorporated by reference in their entirety.

The use of spiro orthocarbonate compounds in combination with resins has not been limited to dental resins. Yamamoto et al. in U.S. Pat. No. 4,980,109 (the entire disclosure of which is herein incorporated by reference) describe insert injection molding processes utilizing SOC compounds with various molding resins including various kinds of rubber, such as butadiene, isoprene, nitrile, chloroprene and acrylic rubbers; various elastomers such as polyurethanes, polyester, polyamide, and polyolefin elastomers; various thermoplastic resins such as thermoplastic polyurethane, polyamide, polyester, polycarbonate, polystyrene, polyacrylate, polyvinyl alcohol, polyvinyl acetate, and polyvinyl chloride; and thermosetting resins such as epoxy, phenolic, melamine, and unsaturated polyester resins.

It was in light of the long felt need in the art and the numerous attempts by other researchers to provide a suitable class of monomers which undergo expansion in polymerizable compositions by which the current investigation was undertaken in an effort to develop a new generation of improved monomers which ideally would meet the following criteria:

The monomers should have sufficient reactivity toward free radical addition so that active participation in copolymerizations with monomers, such as methacrylate, is guaranteed;

The monomers should efficiently utilize the available double ring-opening pathway at the temperature in which they are used, especially at ambient or near ambient temperatures, dictated especially by dentistry; and, The monomers should contribute a sufficient glass transition component to the copolymer, through the use of substituents or cross-linking, so that large proportions of such monomers can be utilized to control shrinkage without significantly compromising the overall properties and performance of the resulting materials.

SUMMARY OF THE INVENTION

The new class of monomers of the present invention can be represented by formula (I):

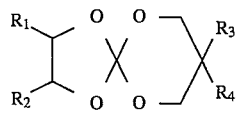

wherein $R_1$ represents a $C_1$–$C_6$ alkenyl, $R_2$ represents hydrogen or $C_1$–$C_6$ alkenyl, $R_3$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; and $R_4$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; formula (II):

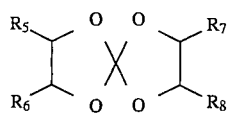

wherein $R_5$ is a $C_1$–$C_6$ alkenyl; $R_6$ represents hydrogen or $C_1$–$C_6$ alkenyl; $R_7$ is a $C_1$–$C_6$ alkenyl or $C_3$–$C_8$ cycloaliphatic unsubstituted, or substituted with halo, $C_1$–$C_6$ alkyl, alkoxy, hydroxy, or one of one or more hetero atoms; or aryl; and $R_8$ is hydrogen or $C_1$–$C_6$ alkyl or a $C_3$–$C_8$ cycloaliphatic unsubstituted, or substituted with halo, $C_1$–$C_6$ alkyl, alkoxy, hydroxy, or one of one or more hetero atoms; or aryl; or formula (III):

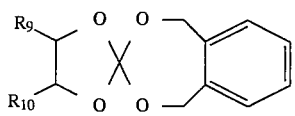

wherein $R_9$ is a $C_1$–$C_6$ alkenyl and $R_{10}$ is hydrogen or lower alkyl. Preferred embodiments of aryl include $C_3$–$C_8$ cyclic radicals, especially $C_6$.

BRIEF DESCRIPTION OF THE DRAWINGS

The sole FIGURE is a partial IR spectra of spiro monomer (A) (top) and its corresponding predominantly ring-opened polymer (bottom).

DETAILED DESCRIPTION OF THE INVENTION

The invention will be further understood by reference to the following five specific monomers (A), (B), (C), (D) and (E) which are representative of the class of monomers according to the invention.

Spiro monomers of the formula (A) and (B):

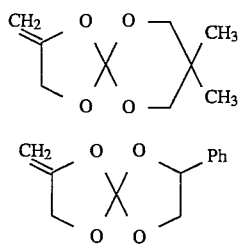

employ an exocyclic methylene group directly attached to one of the strained, spiro linked oxygens.

This activates the carbon-carbon double bond toward free radical addition as compared with the earlier examples of unsaturated spiro orthocarbonates reported in Stansbury et al., (1990), mentioned above, which were similar in nature and reactivity to an alkyl ether model.

In the present invention, reactivity of the spirocyclic monomers toward free radical addition is further enhanced through the preparation of monomers such as (C) and (D).

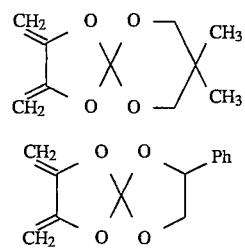

which contain the conjugated diene functionality.

The excellent reactivity associated with the new monomers mean that they can be used in a wide range of proportions with conventional monomers. Indeed, since the monomers of the invention readily crosslink, they yield solid homopolymers without additional comonomers. This is in contrast to previous SOC ring-opened polymers which were viscous oils. Therefore, a sufficient quantity of the SOC monomers could be used to provide zero polymerization shrinkage or a slight volume expansion, if desired, without compromising the mechanical properties of the system. The efficient double ring-opening observed for the polymerization of these monomers should result in the maximum potential volume expansion being realized. This would allow for a greater impact on polymerization shrinkage to be achieved with a smaller proportion of the SOC utilized.

Synthesis

The generalized method used to prepare the asymmetric spiro orthocarbonates of the invention involved the reaction of a cyclic thionocarbonate with a cyclic tin adduct of dibutylic oxide and an appropriate diol. The reaction allows for a variety of ring sizes and substituents and thereby offers control over properties of the monomers and resulting polymers. For monomers (A) and (B), the chloromethyl-substituted cyclic thioncarbonate

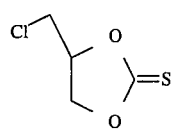

was utilized while with monomers (C) and (D), the roles of the diols were reversed

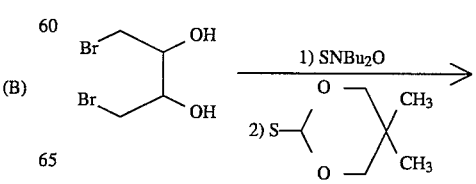

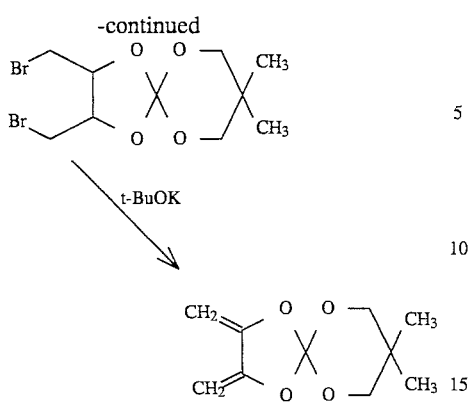

introduce the exocyclic methylene group in monomers (A) and (B) as well as the exocyclic bis(methylene) group in monomers (C) and (D).

Studies with monomer (A) have indicated that several competing polymerization pathways were responsible for the complex structure observed for the homopolymers:

due to instability of the analogous bis(bromomethyl) substituted thionocarbonate. All the spiro orthocarbonate intermediates underwent efficient base-mediated elimination to

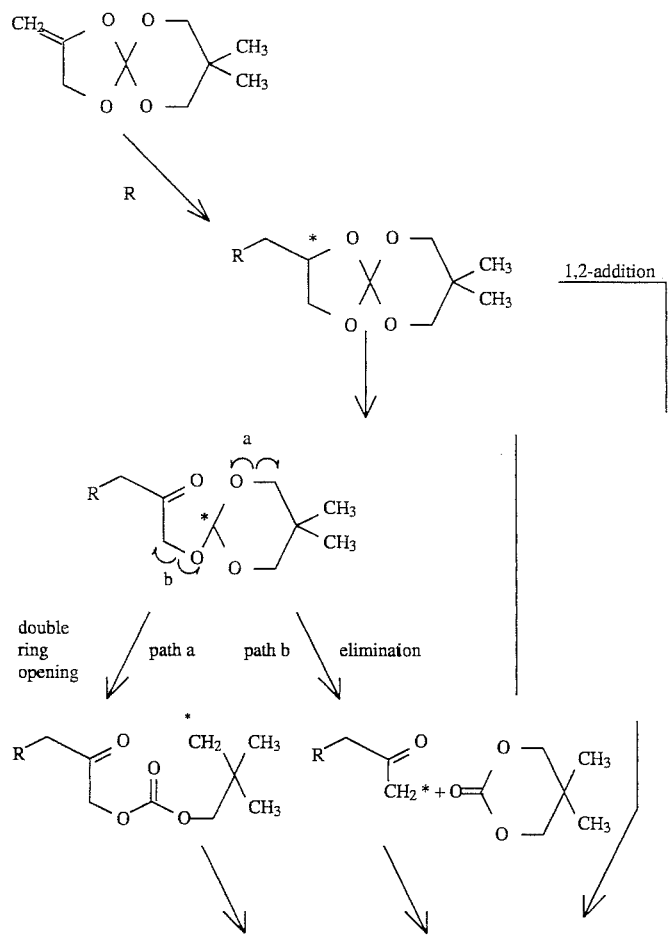

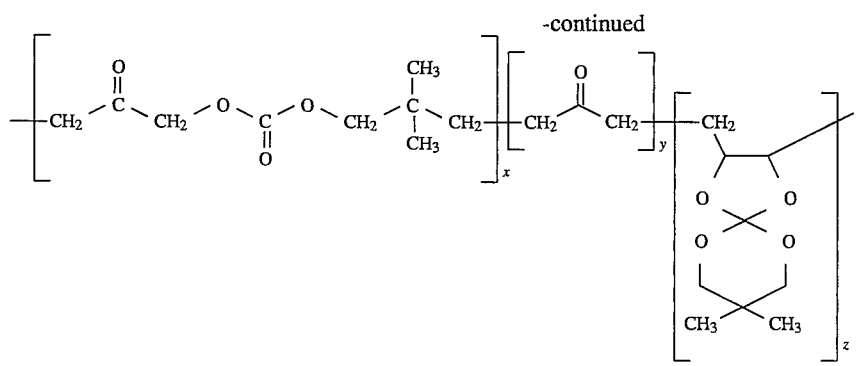

The polymer was comprised of segments resulting from the described double ring-opening along with those from non-ring-opened 1,2-addition polymerization and from single ring-opening with a concomitant elimination of a cyclic carbonate molecule. The elimination pathway accounted for approximately 5 to 15% of the polymer segments from the various polymerization of monomer (A). The corresponding estimates of double ring-opening associated with the polymerizations of monomer (A) varied between 45 and 85% as reported in Table 2 below. While the double ring-opening (path a) and single ring-opening with elimination (path b) both result in the cleavage of two covalent bonds for each addition to the growing polymer chain, the latter is unsatisfactory due to the incorporation of a leachable product into the polymer matrix.

The problem of single ring-opening with elimination encountered in the preparation of monomer (A) prompted the synthesis of monomer (B) which contains a phenyl substituent positioned in an attempt to bias the polymerization in favor of the double ring-opening by offering the potential for a low energy benzylic propagating radical according to the following scheme:

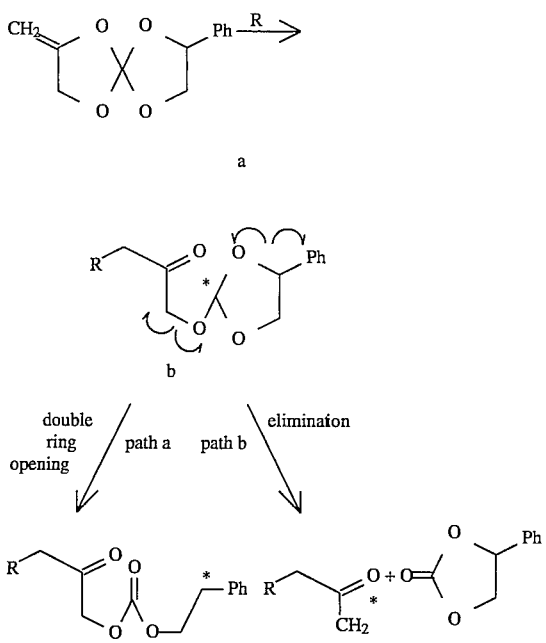

Monomer (E) having the following structure:

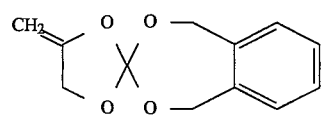

which is related to monomer (B) through its ability to form a stabilized benzylic radical upon double ring-opening, was also prepared. Its relatively high melting point (126°–127° C.) resulted in solubility limitations which precluded its use in dental resin formulations although its utility in other environments is not hindered in any way.

As further exemplification of the properties of the novel class of SOC monomers as compared to a monomer (F) having the structure:

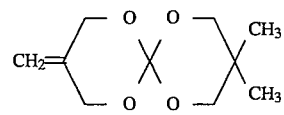

each was synthesized. Monomer (A) of the invention and monomer (F) were each separately free radical 1:1 copolymerized with styrene at 65° C. Monomer (A) produced a copolymer which contained 4% of the spiro component of (A), although none was of the double ring-opened form. Monomer (D) was copolymerized 1:1 with methyl methacrylate at 65° C. The resulting copolymers contained about 75% of the spiro component and significant ring-opening was observed. As compared to monomer (F), in which none of the SOC ingredient was incorporated into the resulting polymerizate, the monomers of the invention were unexpectedly superior. Customary polymerization of SOC monomers occurs at 120°–140° C. Thus, it can be seen that even at significantly lower temperatures, the SOC monomers of the invention will polymerize. Monomers (C) and (D) can readily polymerize at ambient temperatures.

The following examples will further illustrate the invention but it is to be understood that such examples are not intended to be limiting of the invention, which is defined by the appended claims.

EXAMPLE 1

Synthesis of Monomer (B)

All chemicals utilized to produce tile ring-opening monomers were obtained from Aldrich Chemical Co. (Milwaukee Wis.). The spiro orthocarbonates employed were synthesized by techniques similar to that which follows for monomer B:

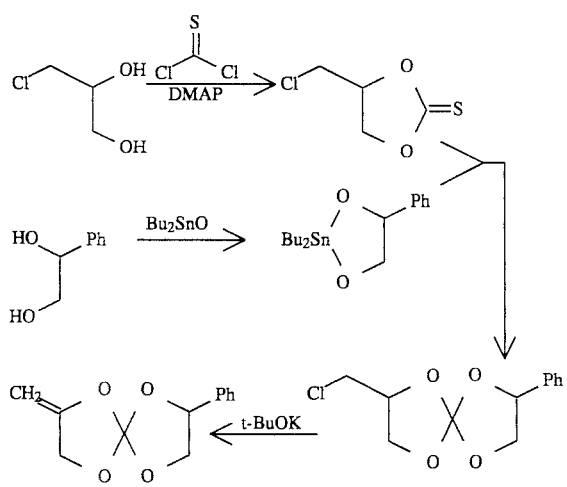

The reaction of 3-chloro-1,2-propanediol with thiophosgene in the presence of 4-N,N-dimethylaminopyridine was used to prepare the prerequisite chloromethyl substituted cyclic thionocarbonate. This reaction was conducted on a 1 mole scale in toluene and provided the aforementioned cyclic thioncarbonate as a white crystalline solid with a melting point of 45°–46° C. in 55% yield. 1-Phenyl-1,2-ethanediol was condensed with dibutyltin oxide in refluxing toluene to form the cyclic tin adduct with liberation of the theoretical quantity of water. The cyclic thionocarbonate was then added in an equimolar proportion at 90° C. to produce a chlorine intermediate which was subjected to de-hydrohalogenation with a two-fold excess of potassium tert-butoxide at room temperature. Vacuum distillation provided monomer (B) as a colorless oil in 33% overall yield from diol in this one pot reaction sequence.

EXAMPLE 2

The free radical polymerization behavior of the new spiro orthocarbonate monomers of the invention was investigated through homopolymerizations in bulk (evacuated sealed tubes) and solution (10% by weight in argon saturated chlorobenzene) at 130°±5° C. with di-tert-butylperoxide (DTBP, 2 mole %) as initiator. The resulting polymers were isolated by precipitation from hexane and were characterized by $^1H$ and $^{13}C$ NMR (JEOL GSX-270) as well as IR (Perkin-Elmer 1420) analyses. The sole FIGURE provides the partial IR spectra of spiro monomer (A) (top) and its solution polymer (bottom). The monomer spectrum is characterized by the intense C—O absorption centered at 1215 $cm^{-1}$ associated with the strained tetraoxaspiro linkage. The noticeable decrease in this $CO_4$ band coupled with the appearance of a broad carbonyl absorption (centered at 1750 $cm^{-1}$) and the presence of the carbonate C—O absorption (1260 $cm^{-1}$) demonstrates that high degrees of ring-opening can be attained.

The spiro monomers were formulated with an ethoxylated bisphenol A dimethacrylate (EBPADM; Diacryl 101, Akzo Chemie America) in equimolar proportions. For comparison, formulations composed of EBPADM or equimolar amounts of EBPADM and 1,6-hexanediol dimethacrylate (HDDM; Esschem, Essington, Pa.) were also prepared. All resins were activated with 0.2 wt % camphorquinone and 0.7 wt % ethyl 4-dimethylaminobenzoate as the visible light photo-initiation system.

Composites were prepared by mixing four parts of 0.5% A-174 silane (Union Carbide, Danbury, Conn.) treated glass (Corning 7724, 325 mesh, Corning, N.Y.), as filler, with the resin. Diametral tensile strength (DTS) specimens (3×6 mm) were obtained by irradiating the various composites between glass slides with a visible light source (Prismetics Lite, L. D. Caulk Div. of Dentsply, Milford, Del.) for 40 sec per side. The cured specimens were stored in water at 37° C. for 24 h and then loaded to failure on an Instron testing machine at a crosshead rate of 1 cm/min in accordance with ADA Specification No. 27. Statistical significance of the results was determined at the 95% confidence level.

Results

Details of the synthesis and characterization of the spirocyclic monomers are given in Table 1.

TABLE 1

Synthesis and Characterization of Spiro Orthocarbonates

| Monomer | Yield, %[a] | mp, °C. | IR, $cm^{-1}$ C=C | $^{13}C$ NMR, δ $CO_4$ |
|---|---|---|---|---|
| A | 76 | 20 | 1698 | 125.3 |
| B | 33 | oil | 1698 | 135.3[b] |
| C | 30 | 67–68 | 1689, 1650 | 123.9 |
| D | 31 | oil | 1688, 1658 | 133.6 |

[a]Overall yield of two-step reaction.
[b]Pair of signals at δ 135.28 and 135.33 due to a mixture of diastereomers.

The relatively high yield reported for monomer (A) was the result of optimization of the reaction conditions over several attempts. The yields given for the other spirocyclic monomers represent the initial synthetic attempts utilizing conditions similar to those devised for monomer (A).

In general, the relative tendencies of the spiro monomers to engage in free radical polymerization can be assessed from the observed yields of polymer obtained from the homopolymerization studies (Table 2).

TABLE 2

Homopolymerization of Spirocyclic Monomers

| | Polymer Yield, %[a] | | Double Ring |
|---|---|---|---|
| Monomer | bulk | solution | Opening, % |
| A | 20 | 24 | 45–85 |
| B | 49 | 34 | 50–80 |
| C | 100 | 86 | 60–85 |
| D | 100 | 78 | 50–70 |

[a]Yields were determined gravimetrically and represent the average from several polymerization runs.
[b]The ranges of the estimated values given are from the bulk polymerizations.

Monomers (A) and (B) furnished only soluble polymers while the bulk polymerizations of monomers (C) and (D) gave exclusively cross-linked polymers. Solution polymerizations involving monomers (C) and (D) did provide small amounts of soluble polymer along with larger proportions of cross-linked materials. The IR and NMR spectra of the polymer samples were evaluated to make an estimation of the degree of ring-opening achieved for each of the different monomers.

The spirocyclic monomers (A), (B) and (D), which were liquids at room temperature, were formulated with EBPADM to obtain the experimental resins to be compared with the all-methacrylate controls. The composition of these formulations and the corresponding DTS values of the cured composites are given in Table 3.

TABLE 3

Diametral Tensile Strength of Dental Composites

| Formulation | Weight % | DTS, MPa ± sd[a] | Comments |
|---|---|---|---|
| EBPADM | 100 | 49.4 ± 2.3 (6) | photo-cure |
| EBPADM | 100 | 44.4 ± 2.1 (6) | dual-core |
| EBPADM/HDDM | 65.2/34.8 | 46.0 ± 3.3 (5) | photo-cure |
| EBPADM/HDDM | 65.2/34.8 | 45.1 ± 4.6 (5) | dual-core |
| EBPADM/(A) | 71.9/28.1 | 34.9 ± 1.7 (6) | photo-cure |
| EBPADM/(A) | 71.9/28.1 | 40.6 ± 0.8 (6) | evacuated |
| EBPADM/(A) | 71.9/28.1 | 47.4 ± 1.7 (6) | dual-core |
| EBPADM/(A) | 71.9/28.1 | 47.8 ± 1.0 (6) | chemical-cure |
| EBPADM/(B) | 68.4/31.6 | 50.4 ± 2.8 (6) | dual-core |

[a]Numbers in ( ) indicate the number of samples.

These results indicate that the initiation method and the polymerization conditions exercise appreciable control over the efficiency of the spiro monomer polymerization.

The improved yields observed for polymers obtained from monomer (B) compared with those from monomer (A) would at first appear to indicate that the addition of the radical-stabilizing phenyl substituent favored the double ring-opening. This would follow since any significant contribution from an elimination pathway would serve to limit the apparent polymer yield. However, upon analysis of the structure of polymers provided by monomer (B), the degree of double ring-opening and the percent of elimination appeared to be roughly the same as for polymers of monomer (A). One possible benefit associated with the more hydrophobic nature of monomer (B) compared with (A) may be enhanced hydrolytic stabilities of the monomer and eventual polymers.

The bis(methylene)-substituted spiro compounds (C) and (D) proved to be extremely reactive monomers. Polymerization in bulk provided clear, glassy polymers with no residual monomer present. In contrast to other unsaturated spiro orthocarbonates previously examined (Stansbury, "Free Radical Ring-Opening Polymerization of Unsaturated, Asymmetric Spiro Orthocarbonates, Ph.D. thesis, University of Maryland, College Park, 1988), monomers (C) and (D) underwent thermal polymerization without initiator at temperatures as low as 85° C. Moreover, extensive polymerization of monomer (D) was noted on exposure of an unactivated sample to a sunlamp for 30 min.

Structural analysis of polymers produced from monomer (C) revealed that double ring-opening was prevalent even at low temperatures and that the pathway involving single ring-opening with elimination was still present. Some of the monomer was incorporated into the polymer as intact spiro orthocarbonate units, presumably through 1,4-diene addition since no evidence of 1,2-addition was observed in the soluble polymer samples. The actual structure of the polymers derived from the bis (methylene) spiro monomers has not been determined as yet, but the double ring-opened, linear carbonate linkage was apparently present in significant proportions.

The solution polymerization of these spiro monomers always provided the highest percentages of double ring-opening. This would be expected since unlike the bimolecular 1,2-addition, the unimolecular ring-opening isomerization should not be adversely influenced by a decrease in monomer concentration. There was considerable variation in the extent of ring-opening observed for similar polymerizations of each of the monomers. The broad ranges obtained severely restrict the interpretations that can be drawn from the results. The small monomer quantities utilized (typically 0.2–0.5 g per polymerization) inherently cause difficulty in regulation of initiator levels. The potential of trace impurities to profoundly effect the polymerization outcome should also be recognized and perhaps systematically examined.

The DTS values of experimental dental composites were used as a preliminary evaluation of the polymerization efficiency of the spiro monomers and their compatibility with methacrylate-based comonomers. All the resins were of suitable viscosity for use in dental composite applications. The standard photo-cure of the experimental composites provided the lowest mechanical strength properties (Table 3). This characteristic was also noted in previous work with other spiro orthocarbonate monomers used in dental composite applications (Stansbury, 1990), mentioned above. Utilizing the formulation with spiro monomer (A), the effect of varied polymerization methods and conditions on DTS of the composites was examined. The refractive indices of the novel monomers (Table 4) appear to be generally consistent with those of conventional monomers. This would appear to eliminate a refractive index mismatch between resin and filler as the source of the relatively low mechanical strength properties associated with the photo-cured, spiro-based materials.

TABLE 4

Refractive Indices of Liquid Spiro Monomers

| Monomer | Refractive Index $n_d^{22}$ |
|---|---|
| (A) | 1.4585 |
| (B) | 1.5302 |
| (C) | 1.5418 |

Alternatively, the low photo-cured DTS values might possibly be explained by the build-up of excessive amounts of oxygen in the resin as a result of the presence of the spiro orthocarbonate functionality. The photo-cure polymerization process may be more prone to oxygen inhibition than the chemical-cure route. The uncured composite containing monomer (A) was evacuated to ca. 5 Pa for 2 h and then purged with argon. The specimens then immediately underwent the normal photo-curing procedure. This resulted in a significant increase in the DTS compared with the non-evacuated experimental formulation.

The composite formulation including spiro monomer (A) was also subjected to a dual-cure polymerization process, that is, a rapid photo-cure in conjunction with a slow chemical-cure as a consequence of using 1 wt % benzoyl peroxide-coated filler. This technique produced a substantial, highly significant improvement in the DTS compared with the initial photo-cure result. This increase is interesting since there were no significant changes in the strength properties of the two control formulations upon application of the dual-cure technique. The addition of an efficient tertiary aromatic amino accelerator (N, N-dihydroxyethyl-p-toluidine, 0–18 wt %) to the experimental resin and the use of the peroxide-treated glass provided a rapid chemical-cure (2.5 min setting time) and a DTS value that was virtually identical to that from the dual-cure.

From the results in Table 3, it is evident that there are polymerization conditions under which the mechanical strength properties of the experimental materials can match those of the conventional dental resins. This can be contrasted with prior results with less reactive spiro monomers where the DTS values were at best, 10 to 15% below those of the controls (Stansbury, 1990 (discussed above)). In these examples, the dual-cured formulation based on the phenyl-substituted spirocyclic monomer (B) gave a DTS value which was even slightly superior to that of the control formulations, although this difference was not significant. It is notable that these relatively high DTS values can be attained with formulations comprised of large proportions of the monofunctional spiromonomers which do not effectively undergo crosslinking.

What I claim is:

1. A method of preparing a polymerizate from a reactant monomer or prepolymer which undergoes shrinkage during the formation of said polymerizate which comprise reacting said reactant monomer or prepolymer in the presence of a monomer selected from the group consisting of:

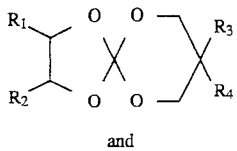

and

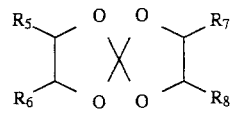

wherein $R_1$ represents a $C_1$–$C_6$ alkenyl, $R_2$ represents $C_1$–$C_6$ alkenyl, $R_3$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; $R_4$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; $R_5$ is a $C_1$–$C_6$ alkenyl; $R_6$ represents $C_1$–$C_6$ alkenyl; $R_7$ is a $C_1$–$C_6$ alkenyl or $C_3$–$C_8$ cycloaliphatic unsubstituted, or substituted with halo, $C_1$–$C_6$ alkyl, alkoxy, hydroxy, or one of one or more hetero atoms; or aryl; and $R_8$ is hydrogen or $C_1$–$C_6$ alkyl or a $C_3$–$C_8$ cycloaliphatic unsubstituted, or substituted with halo, $C_1$–$C_6$ alkyl, alkoxy, hydroxy, or one of one or more hetero atoms; or aryl to form a polymerizate containing said reactant and said monomer as chemically contained constituents thereof.

2. The process of claim 1, wherein the polymerizate of the admixture containing said reactant and said monomer undergoes substantially no shrinkage or positive expansion during the formation of said polymerizate.

3. The process of claim 2, wherein tile reactant monomer or prepolymer comprises an ethoxylated bisphenol of dimethacrylate.

4. The process of claim 2, wherein the reacting step is carried out in the presence of a photo-initiator.

5. The process of claim 4, wherein the photo-initiator is sensitive to visible light.

6. A resinous composition comprising the monomer of formula I

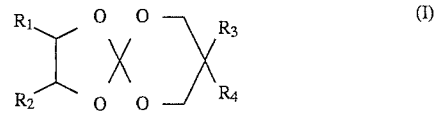

wherein $R_1$ represents a $C_1$–$C_6$ alkenyl, $R_2$ represents $C_1$–$C_6$ alkenyl, $R_3$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; and $R_4$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms and a compound selected from the group consisting of thermoplastic and thermosetting monomer compounds.

7. A composite comprising a polymerized composition of claim 6 and a substrate.

8. A shaped composite comprising a polymerized composition of claim 6.

9. The composite of claim 7, wherein the substrate is embedded within the polymerized composition.

10. The composite of claim 7, wherein the substrate has coated thereon the polymerized composition.

11. The composite of claim 7, wherein there is more than one substrate and the polymerized composite extends between said substrate.

12. Polymers polymerized from the monomers of formula (I):

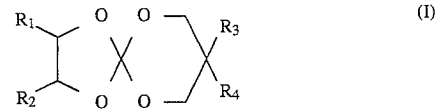

wherein $R_1$ represents a $C_1$–$C_6$ alkenyl, $R_2$ represents $C_1$–$C_6$ alkenyl, $R_3$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms; and $R_4$ represents a $C_1$–$C_6$ alkyl or $C_3$–$C_8$ cycloaliphatic unsubstituted, or substituted with halo, $C_1$–$C_6$ alkyl, alkoxy, hydroxy, or one of one or more hetero atoms.

13. Polymers polymerized from the monomers of formula II

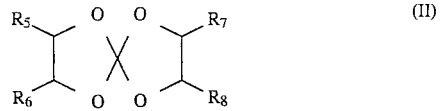

wherein $R_5$ is a $C_1$–$C_6$ alkenyl; $R_6$ represents $C_1$–$C_6$ alkenyl; $R_7$ is a $C_1$–$C_6$ alkenyl or $C_3$–$C_8$ cycloaliphatic unsubstituted, or substituted with halo, $C_1$–$C_6$ alkyl, alkoxy, hydroxy, or one of one or more hetero atoms; or aryl; and $R_8$ is hydrogen or $C_1$–$C_6$ alkyl or a $C_3$–$C_8$ cycloaliphatic unsubstituted, or substituted with halo, $C_1$–$C_6$ alkyl, alkoxy, hydroxy, or one of one or more hetero atoms; or aryl.

* * * * *